United States Patent [19]

Janssen

[11] Patent Number: 4,566,462

[45] Date of Patent: Jan. 28, 1986

[54] VENOUS PRESSURE MEASURING METHOD AND APPARATUS

[75] Inventor: Herbert F. Janssen, Shallowater, Tex.

[73] Assignee: School of Medicine Texas Tech. Univ. Health Servcs. Ctr., Lubbock, Tex.

[21] Appl. No.: 553,951

[22] Filed: Nov. 21, 1983

[51] Int. Cl.$^4$ .......................... A61B 5/02; A61B 10/00
[52] U.S. Cl. ....................................... 128/677; 128/662
[58] Field of Search ......... 128/672, 663, 677, 691–694

[56] References Cited

U.S. PATENT DOCUMENTS

| | | | |
|---|---|---|---|
| 3,099,262 | 7/1963 | Bigliano | 128/2.05 |
| 3,102,534 | 9/1963 | Bigliano et al. | 128/2.05 |
| 3,104,661 | 9/1963 | Halpern | 128/683 |
| 3,123,068 | 3/1964 | Bigliano | 128/2.05 |
| 3,585,987 | 6/1971 | Svensson | 128/2.05 Q |
| 3,605,723 | 9/1971 | King et al. | 128/2.05 M |
| 3,885,551 | 5/1975 | Massie | 128/682 |
| 3,920,004 | 11/1975 | Nakayama | 128/680 |
| 4,027,662 | 6/1977 | Lee | 128/2.05 A |
| 4,030,484 | 6/1977 | Kuska | 128/2.05 R |

OTHER PUBLICATIONS

Guyton, Arthur C., *Textbook of Medical Physiology*, pp. 237–249, 5th ed., 1976, (W. B. Saunders Company, Phila.).

Zagzebski, J. A. et al., "Physics and Instrumentation in Doppler and B-Mode Ultrasonography", from *Introduction to Vascular Ultrasonography*, Ed. Zwiebel, (Grume & Stratton, N.Y., 1982), pp. 1–21.

Wells, P. N. T., "Ultrasoics in Clinical Diagnosis", pp. 156–157, 164–165, Churchill Livingston 1977.

Doriot, P. A. et al., Conf.: Proceedings of the 2d European Congress on UTS in Med., Munich Germany, (May 12–16, 1975), pp. 160–168.

Raines, J. K. et al., "A Non-Invasive Pressure-Pulse Recorder: Development & Rationale", Med. Instrumentation vol. 7, #4, Sep.–Oct. 1973, pp. 245–250.

*Primary Examiner*—Kyle L. Howell
*Assistant Examiner*—Francis J. Jaworski
*Attorney, Agent, or Firm*—Walter C. Farley

[57] ABSTRACT

Venous pressure is measured by monitoring blood flow in a vein with a Doppler probe, exerting pressure on the vein downstream of the probe with a cuff inflated at the rate of 10 mm Hg/second or more and recording the pressure at the instant blood flow stops. The cuff is immediately deflated. Measuring apparatus is also disclosed.

8 Claims, 2 Drawing Figures

VENOUS PRESSURE MEASURING METHOD AND APPARATUS

BACKGROUND OF THE INVENTION

The measurement of blood pressure has become a standard diagnostic test in medicine but the pressure which is normally measured is arterial pressure. The measurement can be made by inserting a catheter into an artery and connecting an inserted tube to a manometer, but is clinically accomplished by exerting pressure from outside of the artery until blood flow stops completely, the exerted pressure being a measure of the systolic pressure; and then detecting when flow is momentarily stopped at the lowest point of the cardiac wave, giving a measure of diastolic pressure. An inflated cuff is normally used to exert the pressure from outside, and the existence or stoppage of flow is sensed by listening with a stethoscope.

While arterial pressure measurements are and will remain important, measurements of venous pressure can indicate the possible existence, progress or incipience of abnormal conditions which are not revealed by arterial measurements alone and is important in the evaluation of patients with congestive heart failure, renal failure, septic shock, traumatic shock, cancer and other illnesses, especially as an aid in fluid management. Unfortunately, measuring venous pressure is more difficult than arterial because the pressure is lower and the variations less distinct and because the flow rate in any readily accessible vein is lower than in an artery of equivalent accessibility. In fact, the variations which do occur are respiratory rather than cardiac. While arterial pressures are in the order of 80 mm Hg (diastolic) to 120 mm Hg or more (systsolic), venous pressure generally lies in the range of about 5 mm Hg tro about 35 mm Hg.

Thus, venous pressure measuring has usually been limited to monitoring the pressure in patients who have a clear need, i.e., whose conditions require the information. In such cases the measurements have been made using invasive techniques, i.e., by inserting a pressure transducer into a vein or by inserting a tube coupled to a pressure measuring device such as a manometer. This is obviously a more sever technique than would be acceptable for normal clinical use and involves risks of infection and blockage.

The following documents include examples of prior devices intended to measure pressures, discussions of the physiological aspects of venous pressure and background information on devices usable in connection with the present invention.

| U.S. Pat. No. | Inventor |
| --- | --- |
| 3,605,723 | King et al |
| 3,123,068 | Bigliano |
| 3,102,534 | Bigliano et al |
| 3,099,262 | Bigliano |
| 4,030,484 | Kuska et al |
| 3,039,044 | Dubsky et al |
| 1,926,748 | MacKenzie et al |
| 3,585,987 | Svensson |
| 1,282,632 | Roesch |
| 3,087,488 | Streimer |
| 4,027,662 | Lee |

PUBLICATIONS

*Textbook of Medical Physiology*, Guyton, Ch. 19, "The Systemic Circulation", pp. 237–249 (W. B. Saunders Co., Phila., 1976, 5th Edition).

*Introduction to Vascular Ultrasonography*, "Physics and Instrumentation in Doppler and B-Mode Ultrasonography", pp. 1–21, Zagzebski et al, 1982.

Reprint from *SURGERY, Gynecology & Obstetrics*, July, 1976, Vol. 143, 23–25, "Differentiation of Superficial Thrombophlebitis from Lymphangitis by Doppler Ultrasound", Barnes et al.

BRIEF SUMMARY OF THE INVENTION

Accordingly, an object of the present invention is to provide a method of measuring venous pressure which is non-invasive and involves substantially no risk to the patient.

A further object is to provide an apparatus for measuring venous pressure in a reliable and repeatable fashion.

Another object is to provide such an apparatus which is simple and can be made in a compact, portable form.

Briefly described, the invention includes a method of measuring venous pressure in a human patient comprising providing a flow responsive transducer capable of generating an electrical signal representative of fluid flow, providing an inflatable cuff capable of exerting pressure on a selected vein until blood flow therein is stopped, inflating the cuff at the rate of at least 10 mm Hz/Sec on a limb of the patient while monitoring the pressure and while holding the transducer adjacent the vein being acted on by the cuff on the other side of the cuff from the heart, observing the pressure exerted by the inflated cuff at the moment fluid flow in the vein stops, and rapidly deflating the cuff.

In another aspect, the invention includes an apparatus for measuring venous pressure in a human patient comprising fluid flow sensor means for producing an electrical signal representative of the flow of liquid through a vein when placed adjacent the skin outside of said vein; means for exerting pressure on said vein to stop liquid flow therein; and means for measuring and recording the pressure applied by said means for exerting when said flow stops; said means for exerting pressure being responsive to the measurement of pressure to stop exerting pressure on said vein for a predetermined short interval and to re-exert pressure thereon for making a new measurement.

In order that the manner in which the foregoing and other objects are attained in accordance with the invention can be understood in detail, particularly advantageous embodiments thereof will be described with reference to the accompanying drawings, which form a part of this specification and wherein:

FIG. 1 is a diagrammatic illustation of the apparatus used in connection with the present invention showing the manner of use; and FIG. 2 is a schematic block diagram of the pneumatic and electrical devices in the apparatus of the invention.

DETAILED DESCRIPTION OF PREFERRED EMBODIMENTS

Figure 1:
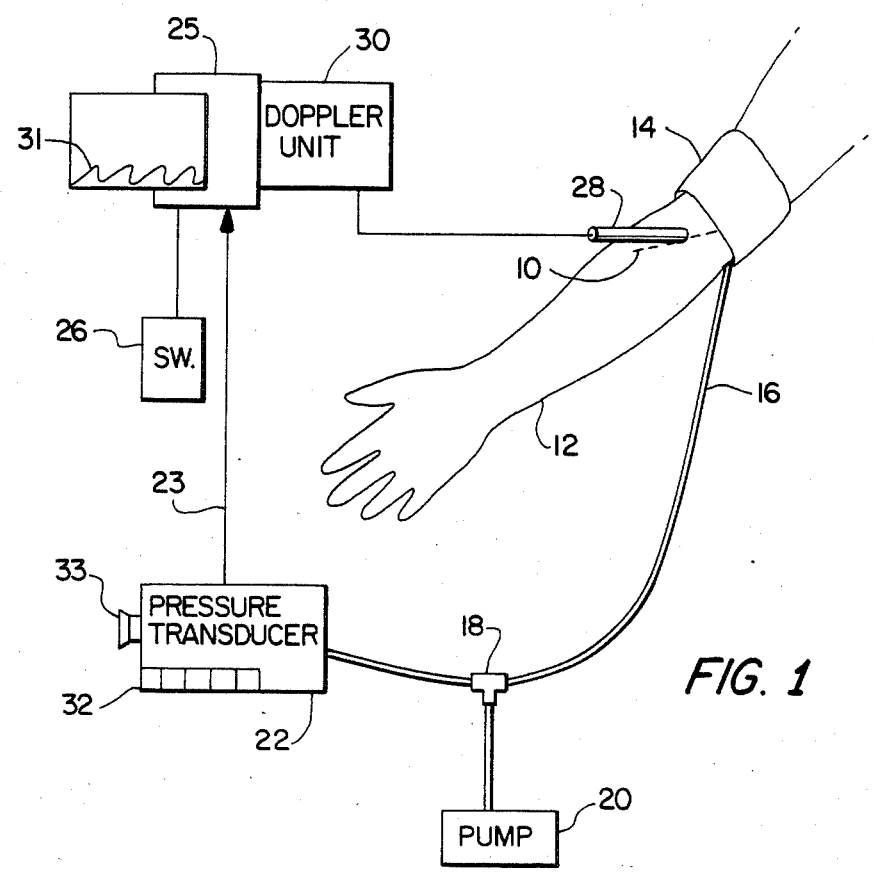

FIG. 1 illustrates the basic apparatus which can be used to accomplish the method of the present invention in measuring the venous pressure. For purposes of illustration, a vein symbolically indicated at 10 in the arm 12 of a patient passes beneath an inflatable cuff 14 which is connected by a pneumatic tube 16 through a T-junction 18 to a pump 20 and to a pressure transducer 22. Transducer 22 has an output cable 33 which provides signals representative of the pressure to a display device which is illustrated as a strip chart recorder 25. The recorder can be conveniently operated by a switch such as a foot switch 26 which allows a physician to actuate the strip chart recorder only when it is needed but without requiring the use of his hands.

A Doppler probe 28 is held adjacent the vein to detect the existence of blood flowing through the vein, probe 28 being connected by a multi-conductor cable to a Doppler control unit 30.

Probe 28 and Doppler unit 30 can advantageously be conventional devices manufactured by MedaSonics, Inc. of Mountainview, Calif., the model D-9 Doppler control unit and the 5 MHz. probe model D-96 manufactured by that company being particularly suitable for this purpose. In addition, the MedaSonics model R12-A chart recorder can be used for recording device 25.

Pressure transducer 22 can be any of a large number of available pressure transducers which respond to a pneumatic input to produce an electrical output signal. Some such devices are provided, or can easily be provided, with a digital display 32 for continuously displaying the pressure input, and can be provided with an audible alarm, synbolically indicated at 33, for sounding an audible indication when the pressure reaches a predetermined level.

Doppler unit 30 ca also be provided with an audio output which is essentially, an audible version of the Doppler signal produced by probe 28. As is well known, A Dopper device such as probe 28 injects a low level of ultrasonic acoustic energy through the body tissue and into the blood stream, this acoustic energy being reflected by irregularities and particles within the stream, the motion of the stream producing a difference in frequency between the transmitted and received signals known as the Doppler frequency. With a 5 MHz. transmission frequency and usual blood flow velocities in the order of 0.1 meters per second, the Doppler frequency is in the vicinity of 400–500 Hz., clearly within the audio range. Thus, the Doppler signal can be amplified or converted into a signal for various processing purposes but can also be listened to directly.

Finally, the pump 20 can be a manually actuated pump such as a resuscitation bag, but it can also be a small electrically driven pump. It is particularly advantageous to have an electrically driven compressor for purposes of venous pressure measurement because it is important to inflate the cuff 14 at a relatively high and known inflation rate. The cuff itself, of course, is a standard blood pressure cuff which is conventionally used for the measurement of arterial pressure.

The method is performed using an appratus similar to that shown in FIG. 1 by placing the inflation cuff on the upper arm and actuating the compressor to inflate the cuff at a rate of 10 mm Hg per second or more and preferably in the range of from about 10 mm Hg/sec. to about 15 mm Hg/sec., while monitoring the flow of blood through vein 10 with probe 28 and simultaneously monitoring the pressure. Inflation of the cuff is terminated upon cessation of venous flow, which usually occurs at a pressure range in the order of about 8 to about 15 mm Hg. The termination of blood flow can be ascertained by listening to the disappearance of the Doppler sound which is quite abrupt.

As soon as venous flow is stopped, the pressure of inflation is noted and the cuff is rapidly and immediately deflated to ambient pressure. It is also necessary to establish an upper limit, in the range of, for example, 50 to 150 mm Hg, at which point the inflation is stopped and the cuff is deflated, regardless of whether flow continues, because elevation of the pressure beyond that level can be dangerous with some patients.

It is desirable to repeat the measurement several times and it is a matter of relatively simple logic and control to provide for automatic inflation, recording of pressure, and deflation of the cuff several times, recording each measurement and reporting the average of the measurements of, for example, four complete measurement cycles in a minute or so.

Figure 2:
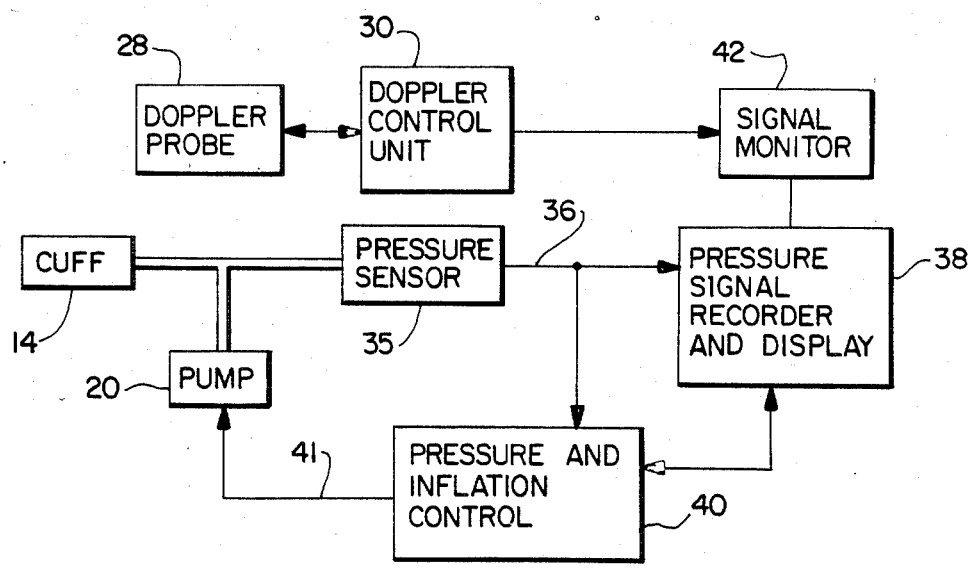

FIG. 2 shows an apparatus which is fundamentally similar to that shown in FIG. 1 but involves some additional sophistication in the nature of automatic control. The Doppler probe 28, control unit 30, cuff 14 and pump 20 can be substantially as described in connection with FIG. 1, the pump in this case being electrically operated. The cuff and pump are connected to a pressure sensor 35 which may or may not be similar to pressure transducer 22, but which produces an electrical output signal on a line 36 representative of the magnitude of the pressure inflating cuff 14. This signal is supplied to a pressure signal recorder and display unit 38 and also to a pressure and inflation control unit 40. Unit 40 supplies a control signal for pump 20 on a line 41 and includes a conventional selector switch arrangement so that a maximum pressure level can be selected above which the cuff should not be inflated. When that pressure level is reached, the signal on line 41 deenergizes the pump and opens a vent valve to cause immediate deflation of the cuff.

The Doppler control unit supplies the Doppler signal to a signal monitor unit 42 which can provide an audible output of the Doppler signal but which also includes amplification and comparison circuitry to accurately detect the existence of a Doppler signal from the probe so that the precise moment of fluid flow termination can be identified. This monitor then produces an output signal to the pressure signal recorder and display unit 38 so that the pressure being measured at that time can be recorded or marked. The marking of the pressure can be accomplished either by placing a mark on the rather sinuous pressure waveform produced on a strip chart recorder such as that illustrated at 31 in FIG. 1 or, if the recorder and display unit is digital, the pressure at that moment can simply be printed or entered into a digital store.

In addition, the recording of a pressure and the identification of the suspension of fluid flow produces a signal for control unit 40 which stops inflation and immediately commences deflation.

As previously mentioned, it is important that the cuff 14 be inflated at a rather rapid rate, not less than about 10 mm Hg/sec. It has been found that slower inflation rates produce artificially high pressure readings by allowing for excessive filling of the veins upstream of the cuff.

The pressure and inflation control unit 40 can also include a cycle timer which initiates a new measurement cycle after a brief pause for cuff deflation. The timer can be set to cause a sequence of a predetermined number of measurements, as previously suggested. A signal indicating the beginning of a new measurement cycle is supplied to the recorder and display unit 38 which, in this arrangement, can also include a simple memory for retaining the previous measurements and an averaging circuit for producing an average of a predetermined number of readings after the timer has gone through its cycles.

The measurement can be accomplished at any conveniently located vein. Preferably one in the arm is chosen because it is easily accessible and is usually at a level equal to that of the heart and the great veins in a bedridden patient. The basilic, cephalic veins or median cubital veins are appropriate choices and are usually free from clotting problems which might alter the venous pressure values obtained.

The recorder and display unit can also be provided with a clock and a digital display for reporting the length of time since the last measurement was taken. The audible output from signal monitor 42, in addition to possibly being useful for detecting the cessation of flow, can be helpful in allowing an operator to accurately place the probe over the selected vein, using the maximum signal as an indication.

While certain advantageous embodiments have been chosen to illustrate the invention it will be understood by those skilled in the art that various changes and modifications can be made therein without departing from the scope of the invention as defined in the appended claims.

What I claim is:

1. A method of measuring venous pressure in a human patient comprising:
   providing a flow responsive transducer capable of generating an electrical signal representative of fluid flow,
   providing an inflatable cuff capable of exerting pressure on a selected vein until blood flow therein is stopped,
   inflating the cuff at the rate of at least 10 mm Hg/Sec on a limb of the patient while monitoring the pressure and while holding the transducer adjacent the vein being acted on by the cuff on the other side of the cuff from the heart,
   observing the pressure exerted by the inflated cuff at the moment fluid flow in the vein stops, and
   rapidly deflating the cuff.

2. A method according to claim 1 which includes using a Doppler transducer as the flow responsive transducer.

3. A method according to claim 2 and including repeating the steps of inflating the cuff, observing the pressure and deflating the cuff a plurality of times, and averaging the pressures observed.

4. A method according to claim 3 and further including the steps of terminating cuff inflation and immediately deflating the cuff without regard to continued flow when the observed pressure reaches a predetermined pressure above the normal range of pressures.

5. A method according to claim 4 wherein said predetermined pressure is between about 50 and about 150 mm Hg.

6. An apparatus for measuring substantially constant venous pressure in a human patient comprising
   fluid flow sensor means for producing an electrical signal representative of the flow of liquid through a vein when placed adjacent the skin outside of said vein;
   means for exerting increasing pressure on said vein to stop liquid flow therein; and
   means connected to said means for exerting pressure for measuring and recording the pressure applied by said means for exerting pressure in rsponse to said signal from said sensor means when said flow stops;
   said means for exerting pressure being responsive to the measurement of pressure to stop exerting pressure on said vein for a predetermined short interval after the pressure is measured and recorded and to re-exert pressure thereon for making a new measurement.

7. An apparatus according to claim 6 wherein said means for exerting pressure includes an inflatable flow occluder and means for inflating said occluder at a substantially constant rate.

8. An apparatus according to claim 7 wherein said rate is between about 10 mm Hg/sec. and about 15 mm Hg./sec.

* * * * *